United States Patent
Johnson, Jr.

(10) Patent No.: US 7,070,998 B2
(45) Date of Patent: Jul. 4, 2006

(54) ADENO-ASSOCIATED VIRUS MATERIALS AND METHODS

(75) Inventor: Philip R. Johnson, Jr., Wynnewood, PA (US)

(73) Assignee: Children's Hospital, Inc., Columbus, OH (US)

( * ) Notice: Subject to any disclaimer, the term of this patent is extended or adjusted under 35 U.S.C. 154(b) by 0 days.

(21) Appl. No.: 11/063,903

(22) Filed: Feb. 23, 2005

(65) Prior Publication Data

US 2005/0169892 A1 Aug. 4, 2005

Related U.S. Application Data

(63) Continuation of application No. 10/263,127, filed on Oct. 2, 2002, now abandoned, which is a continuation of application No. 10/077,294, filed on Feb. 15, 2002, now abandoned, which is a continuation of application No. 09/691,604, filed on Oct. 18, 2000, which is a continuation of application No. 09/292,703, filed on Apr. 15, 1999, now abandoned, which is a continuation of application No. 09/012,132, filed on Jan. 22, 1998, now abandoned, which is a continuation of application No. 08/466,606, filed on Jun. 6, 1995, now abandoned, which is a continuation-in-part of application No. 08/254,358, filed on Jun. 6, 1994, now Pat. No. 5,658,785.

(51) Int. Cl.
C12N 15/35 (2006.01)
C12N 15/63 (2006.01)
C12N 15/64 (2006.01)
C12N 15/864 (2006.01)

(52) U.S. Cl. .................. 435/457; 435/455; 435/456

(58) Field of Classification Search .............. None
See application file for complete search history.

(56) References Cited

U.S. PATENT DOCUMENTS

| 4,797,368 | A | | 1/1989 | Carter et al. ............. 435/320.1 |
| 5,658,785 | A | * | 8/1997 | Johnson .................. 435/367 |
| 5,786,211 | A | * | 7/1998 | Johnson .................. 435/320.1 |
| 5,858,775 | A | * | 1/1999 | Johnson .................. 435/320.1 |
| 6,180,613 | B1 | * | 1/2001 | Kaplitt et al. ............. 514/44 |
| 6,686,200 | B1 | | 2/2004 | Dong et al. ............. 435/457 |

FOREIGN PATENT DOCUMENTS

| WO | WO 91/18088 | 11/1991 |
| WO | WO 93/09239 | 5/1993 |
| WO | WO 93/24641 | 12/1993 |
| WO | WO 95/13365 | 5/1995 |
| WO | WO 95/13392 | 5/1995 |
| WO | WO 95/20671 | 8/1995 |
| WO | WO 95/34670 | 12/1995 |

OTHER PUBLICATIONS

Anderson, Nature, 1998, vol. 392, pp. 25-30.*
Verma et al., Nature, 1997, vol. 389, pp. 239-242.*
Cohen, Science, 1994, vol. 265, pp. 1371-1373.*
Sprent et al., Science, 1994, vol. 265, pp. 1396-1400.*
Glaser, Genetic Engineering News, Jan. 1, 1996, p. 6.*
Rabinovich et al., Science, 1994, vol. 265, pp. 1401-1404.*
Kmiec, American Scientist, 1999, vol. 87, pp. 240-247.
Orkin et al., Report and Recommendations of the Panel to Assess the NIH Investment in Research on Gene Therapy. Dec. 7, 1995.*
Vincent et al., Vaccines 90, 1990, pp. 353-359.*
Kotin, Human Gene Therapy, 1994, vol. 5, pp. 793-801.*
Berkemeier et al., "Neurotrophin-5: A Novel Neuritrophic Factor That Activates trk and trkB", *Neuron* 7:857-866 (1991).
Chatterjee et al., "Dual-Target Inhibition of HIV-1 in Vitro by Means of an Adeno-Associated Virus Antisense Vector", *Science* 258:1485-1488 (1992).
Dixit et al., "Construction and Expression of a Recombinant Adeno-Associated Virus That Harbors a Human β-Globin-Encoding cDNA", *Gene* 104:253-257 (1991).
Dutton, "Gene Therapy Likely to Target Cancer Patients on Larger Scale", *Genetic Engineering News* 14(1):1 and 14-15 (Jan. 15, 1994).
Flotte et al., "Gene Expression from Adeno-associated Virus Vectors in Airway Epithelial Cells", *Am. J. Respir. Cell Mol. Biol.* 7:349-356 (1992).
Flotte et al., "Expression of the Cystic Fibrosis Transmembrane Conductance Regulator from a Novel Adeno-associated Virus Promoter", *J. Biol. Chem.* 268(5):3781-3790 (1993).
Flotte et al., "An improved system for packaging recombinant adeno-associated virus vectors capable of in vivo transduction", *Gene Therapy* 2:29-37 (1995).
Furth et al., "Temporal Control of Gene Expression in Transgenic Mice by a Tetracycline-responsive Promoter", *Proc. Natl. Acad. Sci.* (USA) 91:9302-9306 (1994).
Grima et al., "A Single Human Gene Encoding Multiple tyrosine Hydroxylases with Different Predicted Functional Characteristics", *Nature* 326:707-711 (1987).

(Continued)

*Primary Examiner*—David Guzo
(74) *Attorney, Agent, or Firm*—Marshall, Gerstein & Borun LLP

(57) ABSTRACT

The present invention provides adeno-associated virus (AAV) materials and methods which are useful for DNA delivery to cells. More particularly, the invention provides recombinant AAV (rAAV) genomes, methods for packaging rAAV genomes, stable host cell lines producing rAAV and methods for delivering genes of interest to cells utilizing the rAAV. Particularly disclosed are rAAV useful in generating immunity to human immunodeficiency virus-1 and in therapeutic gene delivery for treatment of neurological disorders.

4 Claims, 5 Drawing Sheets

OTHER PUBLICATIONS

Gossen et al., "Tight control of gene expression in mammalian cells by tetracycline-responsive promoters", *Proc. Natl. Acad. Sci.* (USA) 89:5547-5551 (1992).

Halbert et al., "Adeno-Associated Virus Vectors Transduce Primary Cells Much Less Efficiently than Immortalized Cells", *J. Virol.* 69(3):1473-1479 (1995).

Hermonat et al., "Use of Adeno-associated Virus as a Mammalian DNA Cloning Vector: Transduction of Neomycin Resistance into Mammalian Tissue Culture Cells", *Proc. Natl. Acad. Sci.* (USA) 81:6466-6470 (1984).

Hirsch et al., "An African primate lentivirus ($SIV_{sm}$) closely related to HIV-2", *Nature* 339: 389-332 (1989).

Hirt, "Selective Extraction of Polyoma DNA from Infected Mouse Cell Cultures", *J. Mol. Biol.* 26:365-369 (1967).

Kaplitt et al., "Long-term gene expression and phenotypic correction using adeno-associated virus vectors in the mammalian brain", *Nature Genetics* 8:148-154 (1994).

Karasuyama et al., "Autocrine Growth and Tumorigenicity of Interleukin 2-Dependent Helper T Cells Transfected With IL-2 Gene", *J. Exp. Med.* 169:13-25 (1989).

Kotin et al., "Characterization of a Preferred Site on Human Chromosome 19q for Integration of Adeno-associated Virus DNA by Non-homologous Recombination", *EMBO J.* 11(13):5071-5078 (1992).

LaFace et al., "Gene Transfer into Hematopoietic Progenitor Cells Mediated by an Adeno-Associated Virus Vector", *Virol.* 162:483486 (1988).

Lebkowski et al., "Adeno-Associated Virus: A Vector System for Efficient Introduction and Integration of DNA into a Variety of Mammalian Cell Types", *Mol. Cell. Biol.* 8:3988-3996 (1988).

Levi-Montalcini, "The Nerve Growth Factor 35 Years Later", *Science* 237:1154-1161 (1987).

Lin et al., "GDNF: A Glial Cell Line-Derived Neurotrophic Factor for Midbrain Dopaminergic Neuron", *Science* 260:1130-1132 (1993).

Maisonpierre et al., "Human and Rat Brain-Derived Neurotrophic Factor and Neurotrophin-3; Gene Structures, Distributions, and Chromosomal Localizations", *Genomics* 10:558-568 (1991).

Manthorpe et al., "Ciliary Neuronotrophic Factors", in *Nerve Growth Factors*, 35-56, Wiley & Sons (1989).

Muro-Cacho et al., "Gene Transfer in Human Lymphocytes Using a Vector Based on Adeno-Associated Virus", *J. Immunotherapy* 11:231-237 (1992).

Muzyczka, "Use of Adeno-Associated Virus as a General Transduction Vector for Mammalian Cells" in *Current Topics in Microbiology and Immunology* 158:97-129 (1992).

Podsakoff et al., "Efficient Gene Transfer into Nondividing Cells by Adeno-Associated Virus-Based Vectors", *J. Virol.* 68:5656-5666 (1994).

Puolakkainen et al., "Transforming Growth Factors Alpha and Beta", in *Neurotrophic Factors*, 359-389, Academic Press (1993).

Russell et al., "Adeno-associated virus vectors preferentially transduce cells in S phase", *Proc. Natl. Acad. Sci.* (USA) 91:8915-8919 (1994).

Samulski et al., "Helper-Free Stocks of Recombinant Adeno-Associated Viruses: Normal Integration Does Not Require Viral Gene Expression", *J. Virol.* 63:3822-3828 (1989).

Srivastava et al., "Nucleotide Sequence and Organization of the Adeno-Associated Virus 2 Genome", *J. Virol.* 45:555-564 (1983).

Sumi et al., "Characterization of Recombinant Human Aromatic L-Amino Acid Decarboxylase Expressed in COS Cells", *J. Neurochemistry* 55:1075-1078 (1990).

Tang et al., "Genetic immunization is a simple method for eliciting an immune response", *Nature* 356:152-154 (1992).

Tenenbaum et al., "Adeno-Associated Viruus (AAV) as a Vector for Gene Transfer Into Glial Cells of the Human Central Nervous System", *Gene Therapy 1(Supplement 1)* : S80 (1994).

Tratschin et al., "Adeno-Associated Virus Vector for High-Frequency Integration Expression, and Rescue of Genes in Mammalian Cells", *Mol. Cell. Biol.* 5:3251-3260 (1985).

Ulmer et al., "Heterologous Protection Against Influenza by Injection of DNA Encoding a Viral Protein", *Science* 259:1475-1479 (1993).

Unsicker et al., "Fibroblast Growth Factors: Their Roles in the Central and PeripheraL Nervous System", in *Neurotrophic Factors*, 313-330, Academic Press (1993).

Vincent et al., "Replication and Packaging of HIV Envelope Genes in a Novel Adeno-associated Virus Vector System", *Vaccines* 90:353-359 (1990).

Warner et al., "Intduction of HIV-Specific CTL and Antibody Responses in Mice Using Retroviral Vector-Transduced Cells", AIDS Research and Human Retrovirusus 7:645-655 (1991).

Yu et al., "Progress towards gene therapy for HIV infection", *Gene Therapy* 1:13-26 (1994).

Anderson, "Human Gene Therapy", *Nature*, 392 :25-30 (1998).

Cohen et al., "bumps o n the Vaccine Road", *Science*, 265:1371-1373 (1994).

Glaser et al., "Biotech Firms Shift Focus Toward Therapeutic HIV Vac cine Development", Genetic Engineering News (Jan. 1, 1996).

Kmiec et al., "Gene Therapy", *American Scientist*, 87:240-247 (1999).

Kotin, "Prospects for th e Use of Adeno-Associated Virus as a Vector for Human Gene Therapy", *Human Gene Therapy*, 5:793-801 (1994).

Orkin et al., "Report an d Recommendations of the Panel to Assess the NIH Investment in Research on Gene Therapy"(Dec. 7, 1995).

Rabinovich et al., "Vac cine Technologies: View to the Future", *Science*, 265:1401-1404 (1994).

Sprent et al., "Lympho cyte Life-Span and Memory", *Science*, 265:1395-1399 (1994).

Verma et al., "Gene therapy-promises, problems and prospects", *Nature*, 389:239-242 (1997).

* cited by examiner

ADENO-ASSOCIATED VIRUS MATERIALS AND METHODS

The present application is a continuation of U.S. application Ser. No. 10/263,127, filed Oct. 2, 2002, now abandoned which in turn is a continuation of U.S. application Ser. No. 10/077,294, filed Feb. 15, 2002, now abandoned which in turn is a continuation of U.S. application Ser. No. 09/691,604, filed Oct. 18, 2000, which in turn is a continuation of U.S. application Ser. No. 09/292,703, filed Apr. 15, 1999, now abandoned which in turn is a continuation of U.S. application Ser. No. 09/012,132 filed Jan. 22, 1998, now abandoned which in turn is a continuation of U.S. application Ser. No. 08/466,606 filed Jun. 6, 1995, now abandoned which in turn is a continuation-in-part of U.S. application Ser. No. 08/254,358 filed Jun. 6, 1994 now U.S. Pat. No. 5,658,785.

FIELD OF THE INVENTION

The present invention generally relates to adeno-associated virus (AAV) materials and methods which are useful for delivering DNA to cells. More particularly, the invention relates to recombinant AAV (rAAV) genomes, to methods for packaging rAAV genomes, to stable cell lines producing rAAV and to methods for delivering genes of interest to cells utilizing the rAAV.

BACKGROUND

Adeno-associated virus (AAV) is a replication-deficient parvovirus, the single-stranded DNA genome of which is about 4.7 kb in length including 145 nucleotide inverted terminal repeat (ITRs). See FIG. 1. The nucleotide sequence of the AAV2 genome is presented in Srivastava et al., *J. Virol.*, 45: 555–564 (1983). Cis-acting sequences directing viral DNA replication (ori), encapsidation/packaging (pkg) and host cell chromosome integration (int) are contained within the ITRs. Three AAV promoters, p5, p19, and p40 (named for their relative map locations), drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties which are ultimately responsible for replicating the viral genome. The cap gene is expressed from the p40 promoter and it encodes the three capsid proteins VP1, VP2, and VP3. Alternative and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology*, 158: 97–129 (1992).

When AAV infects a human cell, the viral genome integrates into chromosome 19 resulting in latent infection of the cell. Production of infectious virus does not occur unless the cell is infected with a helper virus (for example, adenovirus or herpesvirus). In the case of adenovirus, genes E1A, E1B, E2A, E4 and VA provide helper functions. Upon infection with a helper virus, the AAV provirus is rescued and amplified, and both AAV and adenovirus are produced.

AAV possesses unique features that make it attractive as a vector for delivering foreign DNA to cells. AAV infection of cells in culture is noncytopathic, and natural infection of humans and other animals is silent and asymptomatic. Moreover, AAV infects most (if not all) mammalian cells allowing the possibility of targeting many different tissues in vivo. Kotin et al., *EMBO J.*, 11(13): 5071–5078 (1992) reports that the DNA genome of AAV undergoes targeted integration on chromosome 19 upon infection. Replication of the viral DNA is not required for integration, and thus helper virus is not required for this process. The AAV proviral genome is infectious as cloned DNA in plasmids which makes construction of recombinant genomes feasible. Furthermore, because the signals directing AAV replication, genome encapsidation and integration are contained within the ITRs of the AAV genome, the internal approximately 4.3 kb of the genome (encoding replication and structural capsid proteins, rep-cap) may thus be replaced with foreign DNA such as a gene cassette containing a promoter, a DNA of interest and a polyadenylation signal. Another significant feature of AAV is that it is an extremely stable and hearty virus. It easily withstands the conditions used to inactivate adenovirus (56° to 65° C. for several hours), making cold preservation of rAAV-based vaccines less critical. Finally, AAV-infected cells are not resistant to superinfection.

Various groups have studied the potential use of AAV in treatment of disease states. Patent Cooperation Treaty (PCT) International Publication No. WO 91/18088 published. Nov. 28, 1991 and the corresponding journal article by Chatterjee et al., *Science*, 258: 1485–1488 (1992) describe the transduction of intracellular resistance to human immunodeficiency virus-1 (HIV-1) in human hematopoietic and non-hematopoietic cell lines using an rAAV encoding an antisense RNA specific for the HIV-1 TAR sequence and polyadenylation signal. The review article Yu et al., *Gene Therapy*, 1: 13–26 (1994) concerning gene therapy for HIV-1 infection lists AAV as a possible gene therapy vector for hematopoietic stem cells. The use of rAAV vectors as a delivery system for stable integration and expression of genes (in particular the cystic fibrosis transmembrane regulator gene) in cultured airway epithelial cells is described in PCT International Publication No. WO 93/24641 published Dec. 9, 1993 and in the corresponding journal article by Flotte et al., *Am. J. Respir. Cell Mol. Biol.*, 7: 349–356 (1992). Gene therapy involving rAAV in the treatment of hemoglobinopathies and other hematopoietic diseases and in conferring cell-specific multidrug resistance is proposed in PCT International Publication No. WO 93/09239 published May 13, 1993; Muro-Cacho et al., *J. Immunol.*, 11: 231–237 (1992); LaFace et al., *Virol.*, 162: 483–486 (1988); and Dixit et al., *Gene*, 104: 253–257 (1991). Therapeutic gene delivery into glioma cells is proposed in Tenenbaum et al., *Gene Therapy*, 1(Supplement 1): S80 (1994).

A relatively new concept in the field of gene transfer is that immunization may be effected by the product of a transferee gene. Several attempts at "genetic immunization" have been reported including direct DNA injection of influenza A nucleoprotein sequences [Ulmer et al., *Science*, 259: 1475–1749 (1993)], biolistic gun immunization with human growth hormone sequences [Tang et al., *Nature*, 356: 152–154 (1992) and infection with retroviral vectors containing HIV-1 gp160 envelope protein sequences [Warner et al., *AIDS RESEARCH AND HUMAN RETROVIRUSES*, 7(8): 645–655 (1991)]. While these approaches appear to be feasible, direct DNA inoculation may not provide long-lasting immune responses and serious questions of safety surround the use of retroviral vectors. The use of AAV for genetic immunization is a novel approach that is not subject to these problems.

An obstacle to the use of AAV for delivery of DNA is the lack of highly efficient schemes for encapsidation of recombinant genomes. Several methods have been described for encapsidating rAAV genomes to generate recombinant viral particles. These methods all require in trans AAV rep-cap and adenovirus helper functions. The simplest involves transfecting the rAAV genome into host cells followed by co-infection with wild-type AAV and adenovirus. See, for example, U.S. Pat. No. 4,797,368 issued Jan. 10, 1989 to Carter and Tratschin, and the corresponding journal article by Tratschin et al., *Mol. Cell. Biol.,* 5(11): 3251–3260 (1985). This method, however, leads to unacceptably high levels of wild-type AAV. Another general strategy involves supplying the AAV functions on a second plasmid (separate from the rAAV genome) that is co-transfected with the rAAV plasmid. See, for example, Hermonat et al., *Proc. Natl. Acad. Sci. USA,* 81: 6466–6470 (1984) and Lebkowski et al., *Mol. Cell. Biol.,* 8(10): 3988–3996 (1988). If no sequence overlap exists between the two plasmids, then wild-type AAV production is avoided as is described in Samulski et al., *J. Virol,* 63(9): 3822–3828 (1989). This strategy is inherently inefficient, however, due to the requirement for three separate DNA transfer events (co-transfection of two plasmids as well as infection with adenovirus) to generate rAAV particles. Large scale production of rAAV by this method is costly and is subject to variations in transfection efficiency.

Vincent et al., *Vaccines,* 90: 353–359 (1990) reports that a cell line expressing rep-cap functions could be used to package rAAV. Such methods still requires transfection of the rAAV genome into the cell line and the resulting titer of rAAV reported was very low (only about $10^3$ infectious units/ml). Dutton, *Genetic Engineering News,* 14(1): 1 and 14–15 (Jan. 15, 1994) reports that Dr. Jane Lebkowski of Applied Immune Sciences manufactures rAAV using chimeric AAV/Epstein-Barr virus plasmids that contain a recombinant AAV genome, the hygromycin resistance gene and the EBV ori P fragment and EBNA gene. The plasmids are transfected into cells to generate stable cell lines. The stable cell lines are then transfected with wild-type AAV rep-cap functions and infected with adenovirus to produce rAAV. Like the method of Vincent, the Lebkowski packaging method requires both transfection and infection events to generate rAAV particles.

There thus exists a need in the art for efficient methods of packaging rAAV genomes and for specific rAAVs useful as vectors for DNA delivery to cells.

SUMMARY OF THE INVENTION

The present invention provides recombinant AAV (rAAV) genomes useful for delivering non-AAV DNA of interest to a cell. The rAAV genomes of the invention include AAV ITRs flanking non-AAV DNA sequences of interest and lack rep-cap sequences encoding functional rep-cap proteins. If it is desirable to express the DNA of interest as a polypeptide in the cell, the rAAV genome also includes a (constitutive or regulatable) promoter and a polyadenylation signal operably linked to the DNA of interest to form a gene cassette. The gene cassette may also include intron sequences to facilitate processing of the RNA transcript in mammalian host cells. A presently preferred gene cassette includes the following DNA segments: (1) the cytomegalovirus (CMV) immediate early promoter, (2) the rabbit β-globin intron, (3) simian immunodeficiency virus (SIV) or human immunodeficiency (HIV) rev and envelope (gp160) genes, and (4) the rabbit β-globin polyadenylation signal. The rAAV genomes of the invention may be assembled in vectors useful for transfection of cells which are permissible for infection with a helper virus of AAV (e.g., adenovirus, E1-deleted adenovirus or herpesvirus). A vector of the invention which contains a rAAV genome including the foregoing preferred gene cassette, a neomycin resistance gene, and wild-type AAV rep-cap sequences was deposited in *E. coli* DH5 cells with the American Type Culture Collection (ATCC), 12301 Parklawn Drive, Rockville, Md. 20852, on Jun. 1, 1994 and was assigned ATCC Accession No. 69637.

Presently preferred rAAV genomes include the SIV rev and envelope (gp160) genes, or the HIV rev and envelope genes, as the non-AAV DNA(s) of interest. Also preferred are rAAV genomes which contain sequences encoding proteins which may ameliorate neurological disorders such as: sequences encoding nerve growth factor (NGF), ciliary neurotrophic factor (CNTF), brain-derived neurotrophic factor (BDNF), neurotrophins 3 and 4/5 (NT-3 and 4/5), glial cell derived neurotrophic factor (GDNF), transforming growth factors (TGF), and acidic and basic fibroblast growth factor (a and bFGF); sequences encoding tyrosine hydroxylase (TH) and aromatic amino acid decarboxylase (AADC); sequences encoding superoxide dimutase (SOD 1 or 2), catalase and glutathione peroxidase; sequences encoding interferons, lymphokines, cytokines and antagonists thereof such as tumor necrosis factor (TNF), CD4 specific antibodies, and TNF or CD4 receptors; sequences encoding GABA receptor isoforms, the GABA synthesizing enzyme glutamic-acid decarboxylase (GAD), calcium dependent potassium channels or ATP-sensitive potassium channels; and sequences encoding thymidine kinase. Also contemplated by the invention are rAAV genomes including globin, oncogene, ras, and p53 sequences. Recombinant AAV genomes including antisense nucleotides that affect expression of certain genes such as cell death suppressor genes (e.g., bcl-2) or that affect expression of excitatory amino acid receptors (e.g., glutamate and NMDA receptors) are also contemplated for modulating neurological disorders.

Other DNA sequences of interest contemplated by the invention include sequences from pathogens including: HIV-1 and HIV-2 (sequences other than rev and gp160 sequences); human T-lymphotrophic virus types I and II; respiratory syncytial virus; parainfluenza virus types 1–4; measles virus; mumps virus; rubella virus; polio viruses types 1–3; influenza virus types A, B and C; non-human influenza viruses (avian, equine, porcine); hepatitis virus types A, B, C, D and E; rotavirus; norwalk virus; cytomegaloviruses; Epstein-Barr virus; herpes simplex virus types 1 and 2; varicella-zoster virus; human herpes virus type 6; hantavirus; adenoviruses; chlamydia pneumoniae; chlamydia trachomatis; mycoplasma pneumoniae; mycobacterium tuberculosis; atypical mycobacteria; feline leukemia virus; feline immunodeficiency virus; bovine immunodeficiency virus; equine infectious anemia virus; caprine arthritis encephalitis virus; and visna virus.

Cell lines of the invention are stably transfected with both rAAV genomes of the invention and with copies of the AAV rep and cap genes. Preferred cell lines are mammalian cell lines, for example, HeLa cell lines. Infection of the cell lines of the invention with AAV helper virus results in packaging of the rAAV genomes as infectious rAAV particles. A presently preferred stable cell line is the A64 HeLa cell line which was deposited with the ATCC on Jun. 1, 1994 and was assigned ATCC Accession No. CRL 11639. The present invention also provides stable cell lines containing AAV rep and cap sequences but no rAAV genome.

Recombinant AAV generated by the foregoing packaging process are useful for delivering the DNA of interest to cells.

In vivo, rAAV may be used as antisense delivery vectors, gene therapy vectors or vaccine (i.e., genetic immunization) vectors. Treatment of disease conditions including, for example, AIDS; neurological disorders including cancer, Alzheimer's disease, Parkinson's disease, Huntington's disease, and autoimmune diseases such as multiple sclerosis, trauma, depression, migraine, pain or seizure disorders; adult T-cell leukemia; tropical spastic paraparesis; upper and lower respiratory tract infections; upper and lower respiratory tract infections; measles; mumps; rubella; polio; influenza; influenza; hepatitis; hepatitis; hepatitis; hepatitis; hepatitis; diarrhea; diarrhea; systemic cytomegalovirus infections; mononucleosis-like illness; systemic Epstein-Barr virus infections; classic infectious mononucleosis; systemic herpes simplex types 1 and 2 infections; genital herpes-simplex infections; chickenpox; roseola; febrile illness due to human herpes virus type 6; pneumonia and adult respiratory distress syndrome; upper and lower respiratory tract infections; conjunctivitis; upper and lower respiratory tract infections; upper and lower respiratory tract infections; genital tract infections; upper and lower respiratory tract infections; pulmonary and extrapulmonary tuberculosis; systemic infections due to atypical, mycobacteria; feline leukemia; feline AIDS; bovine AIDS; equine infectious anemia; arthritis and encephalitis in goats; and pneumonia and encephalitis in sheep are contemplated by the invention. As a vaccine vector, rAAV delivers a gene of interest to a cell and the gene is expressed in the cell. The vaccine vectors may be used to generate intracellular immunity if the gene product is cytoplasmic (e.g., if the gene product prevents integration or replication of a virus). Alternatively, extracellular/systemic immunity may be generated if the gene product is expressed on the surface of the cell or is secreted.

A host (especially a human host) may be immunized against a polypeptide of a disease-causing organism by administering to the host an immunity-inducing amount of a rAAV of the invention which encodes the polypeptide. Immunization of a human host with a rAAV of the invention involves administration by inoculation of an immunity-inducing dose of the virus by the parenteral route (e.g., by intravenous, intramuscular or subcutaneous injection), by surface scarification or by inoculation into a body cavity. Typically, one or several inoculations of between about 1000 and about 10,000,000 infectious units each, as measured in susceptible human or nonhuman primate cell lines; are sufficient to effect immunization of a human host. Virus to be used as a vaccine may be utilized in liquid or freeze-dried form (in combination with one or more suitable preservatives and/or protective agents to protect the virus during the freeze-drying process). For gene therapy (e.g., of neurological disorders which may be ameliorated by a specific gene product) a therapeutically effective dose of a rAAV of the invention which encodes the polypeptide is administered to a host in need of such treatment. The use of rAAV of the invention in the manufacture of a medicament for inducing immunity in, or providing gene therapy to, a host is contemplated.

BRIEF DESCRIPTION OF THE DRAWING

Numerous other aspects and advantages of the present invention will be apparent upon consideration of the following detailed description thereof, reference being made to the drawing wherein.

DETAILED DESCRIPTION OF THE DRAWING

The present invention is illustrated by the following examples relating to the production and use of rAAV of the invention. Example 1 describes the construction of a vector including a rAAV genome containing the SIV rev and envelope (gp160) genes, while Example 2 describes the construction of a vector including the AAV rep-cap genes and a neomycin resistance gene. Example 3 sets out the construction of a vector to be used to generate stable cell lines producing rAAV from the vectors described in Examples 1 and 2. The generation of stable cell lines producing rAAV encoding the SIV rev and gp160 proteins is detailed in Example 4. Example 5 sets out a preferred procedure for purifying rAAV from stable cell lines of the invention. Example 6 describes the generation of stable cell lines expressing the AAV rep-cap genes. Example 7 presents results of infection of various mammalian cells and cell lines with the rAAV described in Example 4 which show that gp160 protein is expressed in the infected cells. Example 8 describes the generation of stable cell lines producing a rAAV that includes the β-galactosidase gene as a DNA of interest and that is useful as a positive control virus for expression of a DNA of interest in target cells or tissues. Example 9 presents the results of experiments in which rAAV of the invention was used to express a DNA of interest in vivo. Example 10 describes methods contemplated by the invention for increasing the titer of rAAV produced by stable cell lines.

EXAMPLE 1

Figure 1:
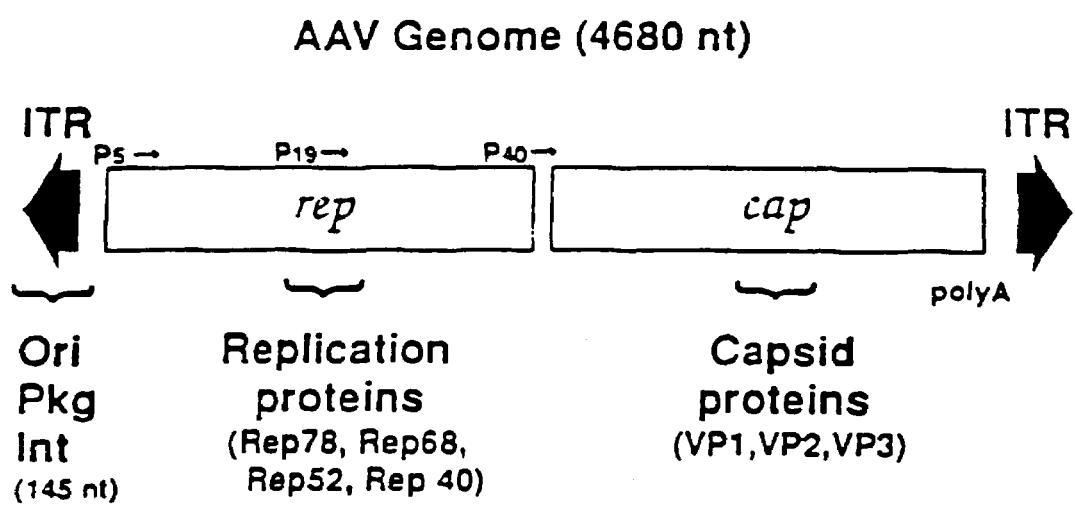
FIG. 1 is a schematic representation of the AAV genome.
Figure 2:
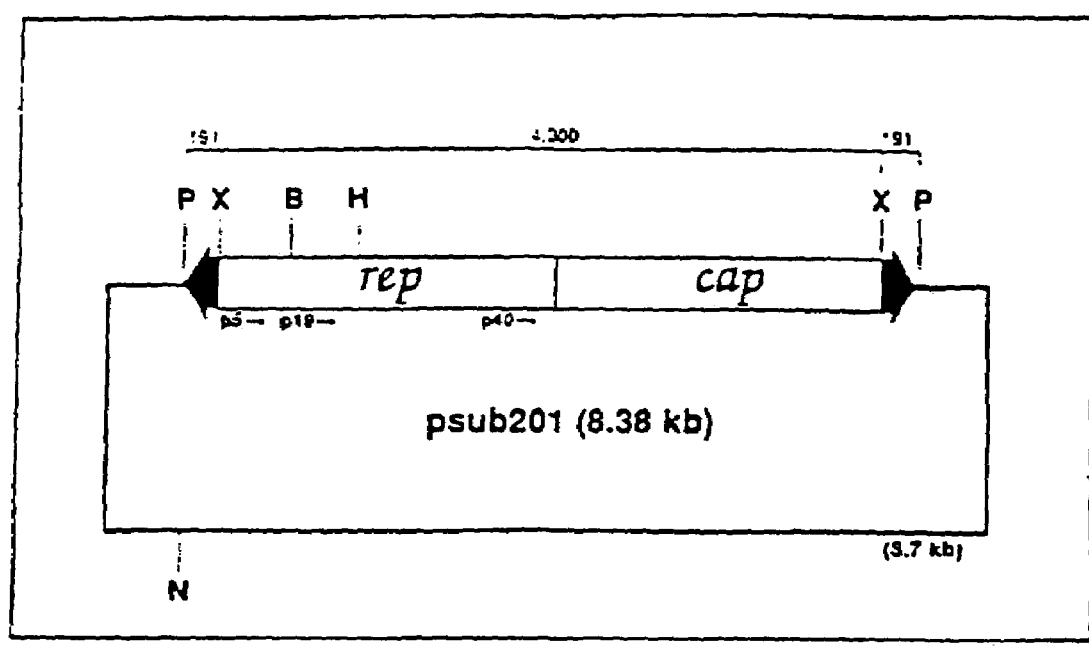
FIG. 2 is a schematic representation of plasmid psub201 which was the source of AAV2 sequences utilized in the examples.

A vector including a rAAV genome containing a SIV rev and envelope (gp160) gene cassette was constructed from an existing plasmid designated psub201 [Samulski et al., supra]. FIG. 2 is a diagram of plasmid psub201 wherein restriction endonuclease sites are shown and abbreviated as follows: P, PvuII; X, XbaI; B, BamHI; H, HindIII; and N, NaeI. The plasmid contains a modified wild-type AAV2 genome cloned between the PvuII restriction sites. The DNA sequence of the wild-type AAV2 genome is set out in SEQ ID NO: 1. The AAV2 sequence was modified to include convenient restriction sites. Specifically, two XbaI restriction sites were added via linker addition at sequence positions 190 and 4484. These sites are internal to 191 bp inverted terminal repeats (ITRs) which included the 145 bp ITRs of the AAV genome. The insertion of these sites allows the complete removal of the internal 4.3 kb fragment containing the AAV rep-cap genes upon XbaI digestion of the plasmid. In FIG. 2, the 191 bp ITRs are designated by inverted arrows.

The rAAV genome vector of the invention (pAAV/CMV/SIVrev-gp160) was generated in several steps.

First, plasmid psub201 was digested with XbaI and the approximately 4 kb vector fragment including the AAV ITRs was isolated. A CMV gene expression cassette was then inserted between the AAV ITRs by blunt end ligation. The CMV expression cassette was derived as a 1.8 kb XbaI—AflIII DNA fragment from the vector pCMV-NEO-BAM described in Karasuyama et al., *J. Exp. Med.*, 169: 13–25 (1989). Prior to ligation, the molecular ends were filled in using the Klenow fragment of DNA polymerase I. The CMV expression cassette contained a 750 bp portion of the CMV immediate early promoter, followed by a 640 bp intron and a 360 bp polyadenylation signal sequence which were derived from the rabbit β-globin gene. Between the intron and poly A sequences were two cloning sites: a unique BamHI site and two flanking EcoRI restriction sites. The resulting vector was named pAAV/CMV. See FIG. 3A wherein restriction endonuclease cleavage sites are shown and abbreviated as follows: B, BamHI; E, EcoRI; N, NaeI; and P, PvuII.

Second, the pAAV/CMV expression vector was linerized at the BamHI site and sticky ends were blunted with Klenow. A PCR-generated, 2.7 kb SIV subgenomic fragment containing the rev and envelope (gp160) sequences [SEQ ID NO: 2, Hirsch et al., *Nature,* 339: 389–392 (1989)] was cloned into the blunt-ended BamHI site. The resulting recombinant AAV genome vector, pAAV/CMV/SIVrev-gp160, is 8.53 kb in length. See FIG. 3B wherein restriction endonuclease cleavage sites are shown and abbreviated as follows: N, NaeI and P, PvuII. The vector contains the following DNA segments in sequence: (1) an AAV ITR, (2) the CMV promoter, (3) the rabbit β-globin intron, (4) the SIV rev and envelope sequences, (5) the rabbit β-globin polyadenylation signal, and (6) an AAV ITR. In transient transfection assays of human 293 cells, this vector resulted in high levels of expression of the SIV gp160 protein as determined by radioimmunoprecipitation assays using polyclonal sera from monkeys infected with SIV.

The invention specifically contemplates substitution by standard recombinant DNA techniques of the following sequences for the SIV rev/envelope sequences in the foregoing vector: HIV-1 rev/envelope sequences (the HIV-1$_{MN}$ rev/envelope sequence is set out in SEQ ID NO: 3); nerve growth factor [Levi-Montalcini, *Science,* 237: 1154–1162 (1987)]; ciliary neurotrophic factor [Manthorpe et al., beginning at p. 135 in *Nerve Growth Factors*, Wiley and Sons (1989)]; glial cell derived neurotrophic factor [Lin et al., *Science,* 260: 1130–1132 (1993)]; transforming growth factors [Puolakkainen et al., beginning at p. 359 in *Neurotrophic Factors*, Academic Press (1993)]; acidic and basic fibroblast growth factors [Unsicker et al., beginning at p. 313 in *Neurotrophic Factors*, Academic Press (1993)]; neurotrophin 3 [Maisonpierre et al., *Genomics,* 10: 558–568 (1991)]; brain-derived neurotrophic factor [Maisonpierre, supra]; neurotrophin 4/5 [Berkemeier et al., *Neuron,* 7: 857–866 (1991)]; tyrosine hydroxylase [Grima et al., *Nature,* 326: 707–711 (1987)]; and aromatic amino acid decarboxylase [Sumi et al., *J. Neurochemistry,* 55: 1075–1078 (1990)].

EXAMPLE 2

A plasmid designated pSV40/neo/rep-cap which contains the AAV rep-cap genes and a neomycin resistance gene was constructed to be used in conjunction with the rAAV genome vector described in Example 1 to generate a stable cell line producing rAAV.

Figure 4:
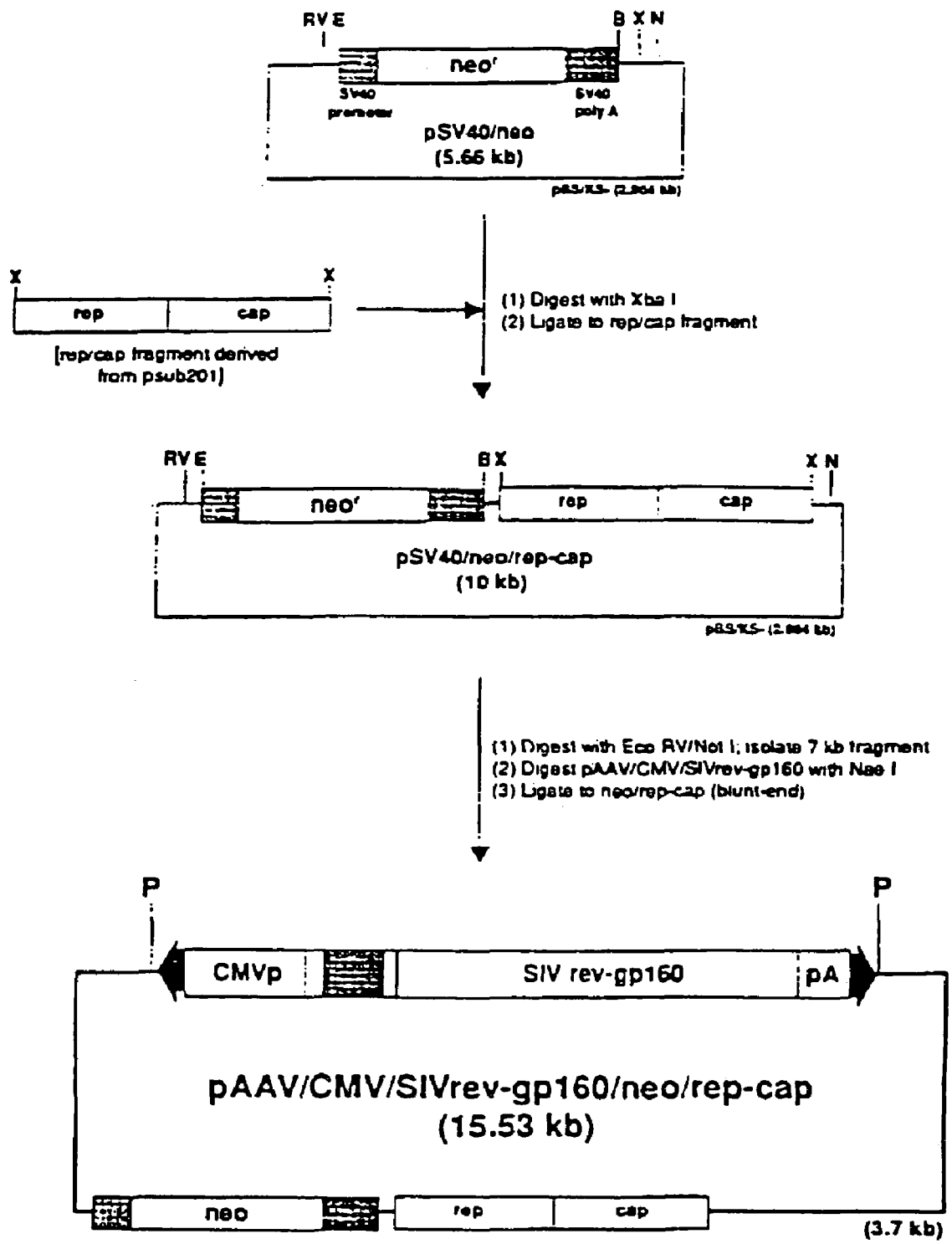
FIG. 4 is a flow diagram of the construction of the vector pAAV/CMV/SIVrev-gp160/neo/rep-cap useful to generate a stable cell line producing rAAV of the invention.

A plasmid designated pAAV/SVneo (Samulski et al., supra) was digested with EcoRI and BamHI to release a 2.7 kb insert including a 421 bp portion of the SV40 early promoter, a 1.4 kb neomycin resistance gene, and a 852 bp DNA fragment containing the SV40 small t splice site and SV40 polyadenylation signal. This released insert was cloned into the EcoRI and BamHI sites of pBLUESCRIP KS+ (Stratagene, La Jolla, Calif.) to generate the 5.66 kb plasmid pSV40/neo. Next, the approximately 4.3 kb DNA fragment containing the AAV rep-cap genes, derived from the digestion of psub201 with XbaI as described in Example 1, was ligated into the XbaI restriction site of pSV40/neo to create the plasmid pSV40/neo/rep-cap (about 10 kb). The construction of this plasmid is detailed in first half of FIG. 4 wherein restriction endonuclease sites are shown and abbreviated as follows: B, BamHI; E, EcoRI; HindIII; P, PvuII; N, NotI; RV, EcoRV; and X, XbaI. This plasmid was functional in transient assays for rep and cap activity and was itself ultimately used to derive stable cell lines (see Example 5 below).

EXAMPLE 3

A final vector to be used to generate stable cell lines producing rAAV was generated from vector pAAV/CMV/SIVrev-gp160 (Example 1) and plasmid pSV40/neo/rep-cap (Example 2).

Figure 3:
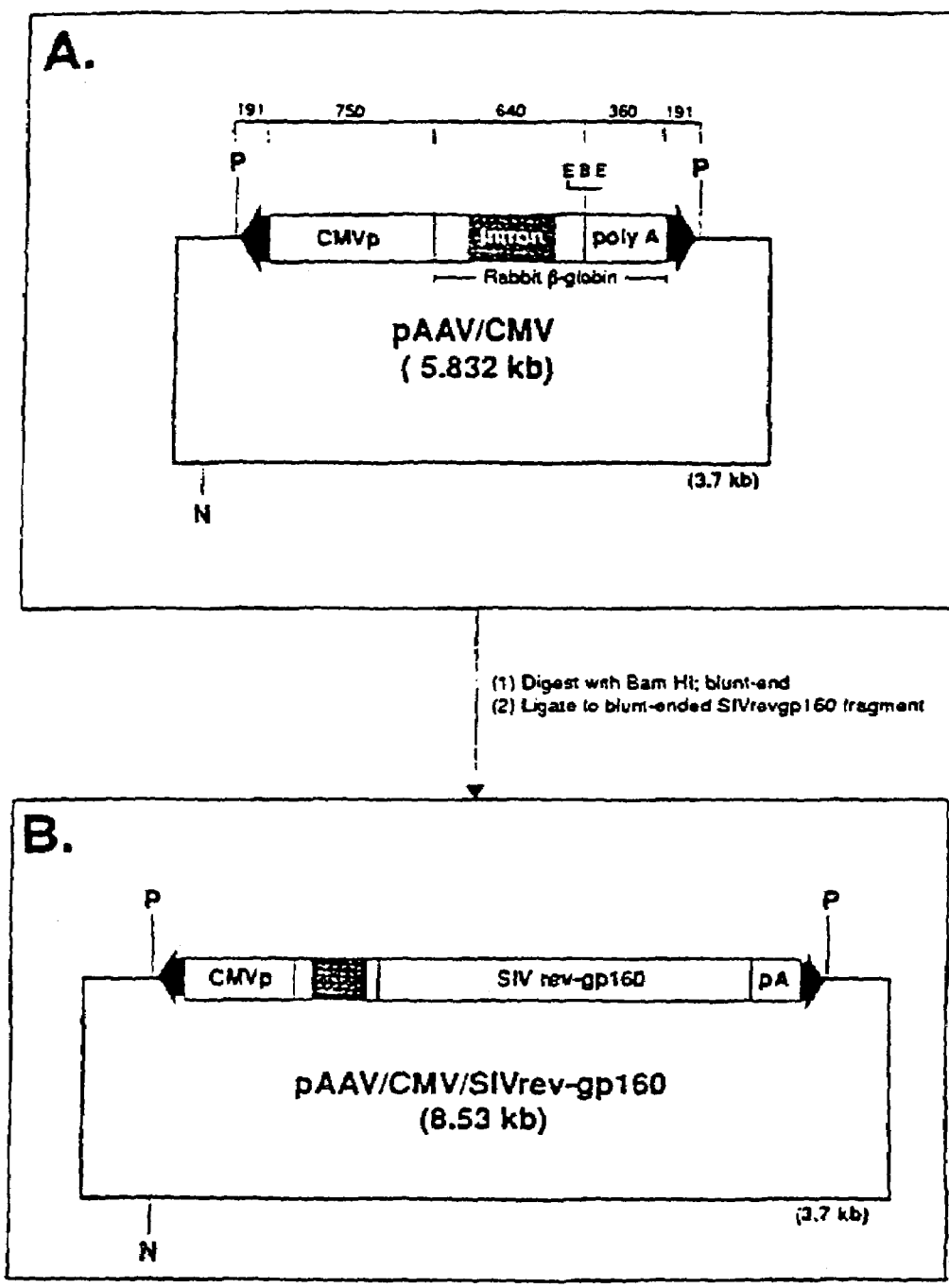
FIGS. 3A through 3B is a flow diagram of the construction of a rAAV genome of the invention in vector pAAV/DMV/SIVrev-gp160.

The construction entailed removing the neo-rep-cap gene cassette from pSV40/neo/rep-cap and inserting it into a unique NaeI site in pAAV/CMV/SIVrev-gp160 (see FIG. 3B). Specifically, vector pAAV/CMV/SIVrev-gp160/neo/rep-cap was made by agarose gel band isolating a 7.0 kb EcoRV-NotI DNA fragment containing the SV/neo and rep-cap expression domains from pSV40/neo/rep-cap. The sticky ends of the fragment were blunted with Klenow and the fragment was ligated into the blunt-ended NaeI site of pAAV/CMV/SIVrev-gp160. See FIG. 4. Vector pAAV/CMV/SIVrev-gp160/neo/rep-cap (ATCC 69637) contains the following elements: (1) the rAAV genome; (2) AAV rep-cap genes; and (3) the neomycin resistance gene.

EXAMPLE 4

The vector pAAV/CMV/SIVrev-gp160/neo/rep-cap was used to generate stable cells lines containing both the rAAV genome of the invention and AAV rep-cap genes.

HeLa cells at 70% confluency were transfected with 10 µg of pAAV/CMV/SIVrev-gp160/neo/rep-cap plasmid DNA in 100 mm dishes. Cells were transfected for 6 hours after formation of DOTAP/DNA complexes in serum minus media as prescribed by the manufacturer's protocol (Boehringer-Mannheim, Indianapolis, Ind.). Following the removal of the transfection medium, DMEM media containing 10% fetal bovine serum was added to the cells. Three days later, media supplemented with 700 µg/ml Geneticin (Gibco-BRL, Gaithersburg, Md.) was used to select for cells that stably expressed the neomycin resistance gene. Fresh Geneticin containing DMEM media was added every four days. Geneticin resistant clones were selected 10–14 days after selective media was added. A total of fifty-five colonies were selected and transferred to 24-well plates and expanded for further analysis.

Figure 5:
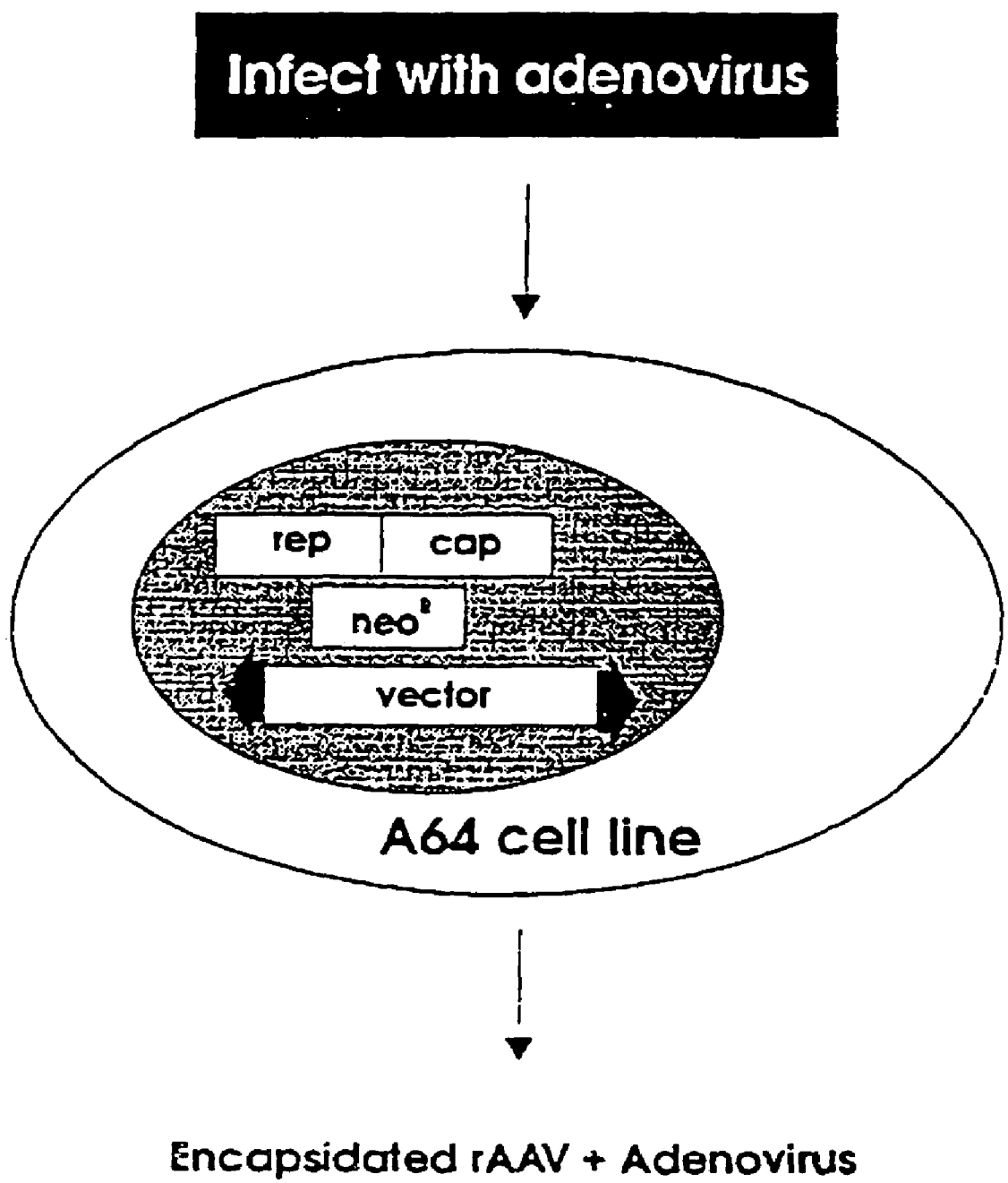
FIG. 5 is a schematic representation of a method for packaging rAAV utilizing stable host cell lines of the invention.

The fifty-five neomycin resistant HeLa cell lines were initially screened for functional rep gene activity; twenty-one scored positive. Rep gene activity was assayed by infecting the cell lines with adenovirus type 5 (Ad5). Infection by adenovirus transactivates the rep and cap genes. This results in the replication of the rAAV genome and subsequent encapsidation of these sequences into infectious rAAV particles. A schematic representation of rAAV production is shown in FIG. 5. Following maximum Ad5-induced cytopathic effect (CPE; rounding of cells and 90% detachment from the culture flask), cell lysates were prepared and Hirt DNA (low molecular weight DNA) was isolated [Hirt, *J. Mol. Biol.*, 26: 365–369 (1967)]. Southern blot analysis was used to visualize the synthesis of recombinant AAV (rAAV) replicative forms (single strand, monomeric, and dimeric forms). Control wells not receiving Ad5 were always negative. Cell lines with high relative levels of rep gene activity were selected for further study.

To assay for cap gene functionality, cell lines were infected with Ad5 and clarified lysates prepared after the development of maximum CPE. The cell lysates, Ad5, and wild-type AAV were used to infect HeLa cells. Following the development of Ad5 induced CPE (72 hr), Hirt DNA was isolated and Southern blot analysis performed. Cell line lysates that gave rise to gp160 hybridizable rAAV (SIV gp160) replicative sequences were scored positive for capsid production.

An infectious unit/ml (IU/ml) titer of rAAV produced by each cell line was derived by co-infecting C12 cells (exhibiting stable rep and cap gene expression) with Ad5 and a serial ten-fold dilution of the clarified cell line lysate to be tested. After maximum Ad5-induced CPE, Hirt DNA was isolated and Southern blot analysis performed to detect the presence of rAAV replicative forms. The end-point dilution that produced visible monomeric and dimeric replication intermediates was taken as the titer. Titer estimation was based on two to four replicate experiments.

Results of characterization of eight of the fifty-five cell lines are shown in Table 1 below wherein "ND" indicates a value was not determined.

TABLE 1

| Cell Line | Rep Function | Cap Function | Titer (IU/ml) |
|---|---|---|---|
| A5  | ++    | + | $10^4$ |
| A11 | ++++  | + | $10^5$ |
| A15 | ++++  | + | $10^5$ |
| A37 | ++++  | + | ND |
| A60 | +++++ | − | $<10^1$ |
| A64 | +++++ | + | $10^6$ |
| A69 | ++    | − | ND |
| A80 | ++++  | + | $10^5$ |

Cell line A64 (ATCC CRL 11639) produced a high titer of rAAV ($10^6$ iu/ml) in clarified lysates. This titer is approximately 1000-fold higher than the titer of rAAV reported by Vincent et al., supra.

The rAAV produced by the various cell lines was also tested for its ability to express SIV gp160 in HeLa cells infected with the recombinant virus. Concentrated stocks of rAAV produced by the eight stable cell lines listed in Table 1 were generated. Cell lysates containing rAAV particles were subjected to step density gradient (CsCl) purification. After desalting dialysis and heat-inactivation of Ad5, the rAAV particles were used to infect (transduce) HeLa cells in culture. Two lines of investigation were pursued. First, the transduced cells were tested for the presence of SIV gp160-specific mRNA by performing RT-PCR on total RNA collected 72 hours after transduction. Primers specific for SIV gp160 amplified a predicted 300 bp fragment only in the presence of reverse transcriptase and Taq polymerase; samples run without reverse transcriptase were uniformly negative. Second, HeLa cells were transduced with various dilutions of the same rAAV/SIV stock as described above and, at 72 hours post transduction, indirect immunofluorescence was performed on the infected cells. At all dilutions tested (out to 1:200), cells positive for the SIV gp160 protein were detected; lower dilutions clearly had more positive cells.

The A64 cell line was tested for wild-type AAV production by a standard method. The cell line was infected with adenovirus to produce rAAV as a lysate. The lysate was then used to infect normal HeLa cells either: (i) alone; (ii) with adenovirus; or (iii) with adenovirus and wild-type AAV. As a control, HeLa cells were infected with adenovirus and wild-type AAV without rAAV. Hirt DNA was prepared and analyzed by Southern blotting (two different blots) for replicating forms of either rAAV or wild-type AAV. No wild-type AAV was detected in A64 cells not exposed to wild-type AAV.

Because the present invention involves the establishment of stable cell lines containing not only copies of the AAV rep and cap genes, but also of the rAAV genome (with ITRs flanking DNA of interest), rAAV is produced by merely infecting the cell line with adenovirus. Transfection of exogenous DNA is not required, thereby increasing the efficiency of rAAV production compared to previously described methods. Other significant features of the invention are that no wild-type AAV is produced and that scale-up for production of rAAV is easy and is limited only by normal constraints of cell growth in culture.

EXAMPLE 5

A method to isolate and purify rAAV from stable (producer) cell lines was developed.

Producer cells (for example, the A64 cells of Example 4) were seeded at a cell density of $3\times10^6$ producer cells per 175 cm$^2$ surface area in growth medium. Cells reached a density of about $8\times10^6$ cells after 16–18 hours, and were then infected with adenovirus (Ad5) at a multiplicity of infection (moi) of 5 for 1–2 hours in growth medium. A 15 ml infection volume was used, and after the 1–2 hour infection, 10 ml of growth medium was added to each flask to obtain a final volume of 25 ml. [Alternatively, Ad5 may be added directly by: removing all but 15 ml of growth medium and adding Ad5 in a volume of 10 ml (diluted in HBSS) to give a final volume of 25 ml.]

Cells were harvested at about 48–60 hours after infection when most cells released from the flask after a vigorous shake. The cells were then stained with trypan blue to determine the percentage of viable cells. It is desirable for greater than 80% to be viable. Cells were then transferred to 250 ml disposable conical bottles (Corning) and pelleted at 1000×g for 15 minutes at 4° C. The resulting supernatant was removed saving an aliquot and the cells were suspended in TM buffer (50 mM Tris, pH 8.0, and 1 mM MgCl$_2$) at a density of $5\times10^6$ cells/ml. The cells were subjected to three cycles of freeze/thaw on dry ice with vortexing 2 minutes between each thaw. The lysed cells were than heated to 56° C. for 30 minutes to 1 hour with vortexing every 7.5 minutes during the last thaw. Ten percent deoxycholate was added to the lysate to a final concentration of 1%, and the mixture was incubated at 37° C. for 30 minutes with intermittent vortexing to achieve complete lysis. If necessary to achieve complete lysis, the mixture was sonicated 3 times on maximum setting for 2 minutes each time. A hemocytometer was used to confirm complete cell lysis. Cell debris was pelleted at 2000×g for 15 minutes at 4° C. The rAAV containing supernatant was saved.

The rAAV was isolated using a 1.31 g/ml CsCl cushion. Twenty-one ml of lysate supernatant was layered on a 14 ml CsCl cushion in a SW-28 tube, and spun 16,000 rmp, 10° C. for 16 hours. The resulting supernatant was aspirated and the rAAV pellet was washed with HBSS to remove residual CsCl. The pAAV pellet was re-dissolved in 20 mM Tris pH 8, 150 mM NaCl, 1 mM $MgCl_2$ (TMN buffer) in the smallest volume manageable (about 500 µl/pellet) and let hydrate overnight. It was then heated to 56° C. for 30 minutes with vortexing every 5 minutes. At this endpoint, the virus was dialyzed against the TMN buffer to remove all traces of cesium if the virus was not going to be further purified.

The rAAV may be further purified by isopycnic banding. This is appropriate under conditions in which the virus is to be administered in vivo. The hydrated rAAV was brought up to a CsCl density of 1.41 g/ml, and then spun in an SW-41 tube at 30K for 48 hours at 10° C. The top portion of the gradient containing adenovirus (density 1.34–1.36 g/ml) was discarded and the remaining portion of the CsCl gradient was diluted with TMN down to a buoyant density of less than 1.1 g/ml. rAAV was then pelleted by an overnight spin at >60,000×g. The rAAV was resuspended in a minimal amount of TMN buffer supplemented with 1% gelatin. For efficient hydration, the pellet was allowed to sit overnight at 4°. The rAAV was then aliquoted and stored at 20° C.

EXAMPLE 6

Concurrent with the generation of the stable cells described in Example 4, stable HeLa cell lines were established by similar methods which contained rep-cap genes but no rAAV genome using plasmid pSV40/neo/rep-cap (Example 2). A total of fifty-two neomycin resistant HeLa cell lines were isolated and characterized.

To test for rep gene function, each cell line was infected with Ad5 and subsequently transfected with pAAV/CMV/SIVrev-gp160. Following Ad5-induced CPE (72 hr), Hirt DNA was isolated and Southern blot analysis performed. Rep gene function was scored positive for cell lines that produced monomeric and dimeric rAAV gp160 sequences. The intensity of autoradiographic signal was used as a relative measure of rep gene expression (1–5+). Ad5 minus control samples never produced rAAV replicative forms. Cap gene proficiency was assayed in a similar manner (Ad5 infection and pAAV/CMV/SIVrev-gp160 transfection), except that a clarified cell lysate was prepared after the development of maximum CPE. HeLa cells were then co-infected with a portion of the clarified cell lysate, Ad5, and wild-type AAV. Hirt DNA was isolated 72 hours later, and hybridization analysis was used to visualize the existence of rAAV/gp160 replicative forms (monomeric and dimeric). In the assay described, the C12 cell line yielded the highest relative proportion of rAAV/gp160/120 sequences.

Results of the characterization assays are presented for eight cell lines are presented in Table 2 wherein the abbreviation "ND" indicates that a value was not determined.

TABLE 2

| Cell Line | Rep Function | Cap Function |
|---|---|---|
| C2 | +++++ | + |
| C12 | ++++ | +++ |
| C16 | − | ND |
| C18 | +++ | ND |
| C23 | +++ | ND |
| C25 | +++ | − |
| C27 | ++ | ND |
| C44 | ++++ | + |

There are two principal uses for the stable cell lines expressing rep-cap sequences: (1) generating rAAV particles if the cell lines are transfected with a rAAV genome and infected with helper virus; and (2) determining rAAV infectious titers. To estimate rAAV infectious titers, these cell lines are co-infected with adenovirus and serial dilutions of the rAAV stock. After maximum CPE, Hirt DNA is isolated and replicative rAAV forms are visualized by Southern blot analysis. End point titration (last rAAV stock dilution to give positive hybridization signal) is then used to determine the infectious titer.

EXAMPLE 7

The ability of the rAAV produced by HeLa cell line A64 to infect (transduce) and produce SIV gp160 protein in various mammalian cell types in addition to HeLa cells (see Example 4) was assayed. The rAAV (at a multiplicity of infection of approximately 1) was used to infect cells either in a monolayer or in suspension, depending on the cell type. Three days after rAAV infection, the cells were fixed in acetone/methanol and evaluated for the production of gp160 by indirect immunofluorescence using polyclonal antisera from an SIV-infected monkey. The following cells or cell lines were infected and shown to produce gp160; fetal rat brain cells (neurons and glial cells), mouse 3T3 fibroblasts, mouse vagina, human vagina, human colon, human and monkey lymphocytes and 293 cells. No non-permissive cell type was identified. These results demonstrate that the rAAV produced by the A64 cell line infects a wide range of mammalian cell types and leads to cell surface expression of the SIV envelop gene product, gp160, in the transduced cells.

EXAMPLE 8

Stable cell lines were generated that produced rAAV carrying the β-galactosidase gene as a gene of interest. These rAAV are useful as positive control to test for expression of a DNA of interest in a target cell or tissue.

A vector like pAAV/CMV/SIVrev-gp160/neo/rep-cap was constructed that included a β-galactosidase gene expression cassette (Clontech, Palo Alto, Calif.) containing the human CMV promoter, the *E. coli* β-galactosidase gene, and the SV-40 splice/polyadenylation sequence instead of the rabbit β-globin intron, SIV rev and envelope sequences, and rabbit β-globin polyadenylation signal between the AAV ITRs. This β-galactosidase gene expression cassette was cloned in between the AAV ITRs by standard recombinant methods.

Stable HeLa cell lines which produced rAAV containing the β-galactosidase gene (rAAV/β-gal) were generated as described in Example 4 using the foregoing vector.

EXAMPLE 9

The rAAV/β-gal of Example 8 were used to demonstrate the use of rAAV of the invention for gene transfer into the brains of live mice. rAAV/β-gal was injected directly into the brains of mice and the brains were then examined for evidence of β-galactosidase activity.

Balb/c mice (n=3; male; 9 months old) were anesthetized and secured on a murine stereotactic platform. Using sterile technique, rAAV/β-gal (1 µl containing $3 \times 10^6$ infectious units) was injected into the right hippocampus. Additional mice (n=3) received an injection of diluent as controls. One week after injection, mice were sacrificed by cardiac exsanguination followed by sequential infusion of 50 ml of heparinized phosphate buffered saline, then 50 ml of a mixture of paraformaldehyde (0.5%) and glutaraldehyde (2.5%) in 0.1M phosphate buffer (pH 7.3). Whole brains were removed. post-fixed in the same fixative mixture (2 hours) and frozen in O.C.T. Cryostat sections (10 µm) were placed on poly-L-lysine coated microscope slides and stored at −20° C. Slides were thawed at room temperature, fixed again (5 minutes at 4° C.), washed twice in PBS, and transferred to X-gal stain (a substrate for the enzymatic activity of β-galactosidase). After incubation overnight at 37°, slides were washed twice in PBS, counterstained with nuclear fast red, and examined microscopically for blue-stained cells (cells where β-galactosidase was being expressed).

In the brains of the mice injected with rAAV/β-gal, blue-stained cells in the hippocampus were easily detected upon microscopic examination. In the brains of mice injected with diluent (controls), no blue-stained cells were found.

EXAMPLE 10

Various methods to increase the titer of rAAV generated from stable cell lines which involve providing additional AAV rep and cap genes to the cell lines are contemplated by the invention.

In a first method which demonstrates the usefulness of providing additional rep and cap genes, a producer cell line is transfected with a plasmid containing a helper plasmid carrying AAV rep and cap genes prior to adenovirus infection. Results from experiments in which a rAAV/β-gal producer cell line (H44) was so transfected are presented in Table 3 below.

TABLE 3

| Treatment | Viral Yield | IU/cell | Fold increase |
|---|---|---|---|
| Mock transfection | $7 \times 10^7$ | 7 | 0 |
| 50 µg pBS/rep-cap | $1 \times 10^9$ | 100 | 14 |
| 100 µg pBS/rep-cap | $8 \times 10^8$ | 80 | 11 |
| 150 µg pBS/rep-cap | $1 \times 10^9$ | 110 | 16 |

In a second method, the AAV rep and cap genes are placed on a separate plasmid containing an EBV or BPV origin of DNA replication and a drug resistance marker (hygromycin). The plasmid will be transfected into a producer cell line and new cell lines are then selected on neomycin and hygromycin. This selection pressure will result in stable cell lines which contain both rAAV genomes and multiple copies of the AAV rep and cap genes.

In a third method, the AAV rep and cap genes are cloned into a helper virus genome, for example, into the adenovirus genome in the E3 location under the control of the tetracycline operator.

While the present invention has been described in terms of preferred embodiments, it understood that variations and improvements will occur to those skilled in the art. Therefore, only such limitations as appear in the claims should be placed on the invention.

What is claimed is:

1. A method for producing infectious recombinant adeno-associated virus comprising the step of infecting a mammalian host cell with a helper virus of adeno-associated virus,
wherein the mammalian host cell is stably transfected with a recombinant adeno-associated virus genome and with adeno-associated virus rep-cap genes, and
wherein the helper virus contains adeno-associated virus rep-cap genes inserted in its genome.

2. A method for producing infectious recombinant adeno-associated virus comprising the step of infecting a mammalian host cell with a helper virus of adeno-associated virus,
wherein the mammalian host cell is stably transfected with a recombinant adeno-associated virus genome and with adeno-associated virus rep-cap genes,
wherein the recombinant adeno-associated virus genome comprises adeno-associated virus inverted terminal repeats flanking DNA sequences encoding an immunodeficiency virus protein operably linked to promoter and polyadenylation sequences, and
wherein the helper virus contains adeno-associated virus rep-cap genes inserted in its genome.

3. A method for producing infectious recombinant adeno-associated virus comprising the step of infecting a mammalian host cell with a helper virus of adeno-associated virus,
wherein the mammalian host cell is stably transfected with a recombinant adeno-associated virus genome and with adeno-associated virus rep-cap genes,
wherein the recombinant adeno-associated virus genome comprises adeno-associated virus inverted terminal repeats flanking DNA sequences encoding a polypeptide selected from the group consisting of tyrosine hydroxylase, aromatic amino acid decarboxylase, nerve growth factor, brain derived neurotrophic factor, NT-3, NT-4/5, glial derived neurotrophic factor and fibroblast growth factor, the DNA sequences being operably linked to promoter and polyadenylation sequences, and
wherein the helper virus contains adeno-associated virus rep-cap genes inserted in its genome.

4. A method for producing infectious recombinant adeno-associated virus comprising the step of infecting a mammalian host cell with a helper virus of adeno-associated virus,
wherein the mammalian host cell is stably transfected with a recombinant adeno-associated virus genome and with adeno-associated virus rep-cap genes,
wherein the recombinant adeno-associated virus genome comprises the cytomegalovirus (CMV) immediate early promoter, the rabbit β-globin intron, the human immunodeficiency virus rev/envelope sequences and the rabbit β-globin polyadenylation signal, and
wherein the helper virus contains adeno-associated virus rep-cap genes inserted in its genome.

* * * * *

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 4680 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

```
TTGGCCACTC CCTCTCTGCG CGCTCGCTCG CTCACTGAGG CCGGGCGACC AAAGGTCGCC      60

CGACGCCCGG GCTTTGCCCG GGCGGCCTCA GTGAGCGAGC GAGCGCGCAG AGAGGGAGTG     120

GCCAACTCCA TCACTAGGGG TTCCTGGAGG GGTGGAGTCG TGACGTGAAT TACGTCATAG     180

GGTTAGGGAG GTCCTGTATT AGAGGTCACG TGAGTGTTTT GCGACATTTT GCGACACCAT     240

GTGGTCACGC TGGGTATTTA AGCCCGAGTG AGCACGCAGG GTCTCCATTT TGAAGCGGGA     300

GGTTTGAACG CGCAGCCGCC ATGCCGGGGT TTTACGAGAT TGTGATTAAG GTCCCCAGCG     360

ACCTTGACGG GCATCTGCCC GGCATTTCTG ACAGCTTTGT GAACTGGGTG GCCGAGAAGG     420

AATGGGAGTT GCCGCCAGAT TCTGACATGG ATCTGAATCT GATTGAGCAG GCACCCCTGA     480

CCGTGGCCGA GAAGCTGCAG CGCGACTTTC TGACGGAATG GCGCCGTGTG AGTAAGGCCC     540

CGGAGGCCCT TTTCTTTGTG CAATTTGAGA AGGGAGAGAG CTACTTCCAC ATGCACGTGC     600

TCGTGGAAAC CACCGGGGTG AAATCCATGG TTTTGGGACG TTTCCTGAGT CAGATTCGCG     660
```

```
AAAAACTGAT TCAGAGAATT TACCGCGGGA TCGAGCCGAC TTTGCCAAAC TGGTTCGCGG    720

TCACAAAGAC CAGAAATGGC GCCGGAGGCG GGAACAAGGT GGTGGATGAG TGCTACATCC    780

CCAATTACTT GCTCCCCAAA ACCCAGCCTG AGCTCCAGTG GGCGTGGACT AATATGGAAC    840

AGTATTTAAG CGCCTGTTTG AATCTCACGG AGCGTAAACG GTTGGTGGCG CAGCATCTGA    900

CGCACGTGTC GCAGACGCAG GAGCAGAACA AAGAGAATCA GAATCCCAAT TCTGATGCGC    960

CGGTGATCAG ATCAAAAACT TCAGCCAGGT ACATGGAGCT GGTCGGGTGG CTCGTGGACA   1020

AGGGGATTAC CTCGGAGAAG CAGTGGATCC AGGAGGACCA GGCCTCATAC ATCTCCTTCA   1080

ATGCGGCCTC CAACTCGCGG TCCCAAATCA AGGCTGCCTT GGACAATGCG GGAAAGATTA   1140

TGAGCCTGAC TAAAACCGCC CCCGACTACC TGGTGGGCCA GCAGCCCGTG GAGGACATTT   1200

CCAGCAATCG GATTTATAAA ATTTTGGAAC TAAACGGGTA CGATCCCCAA TATGCGGCTT   1260

CCGTCTTTCT GGGATGGGCC ACGAAAAAGT TCGGCAAGAG GAACACCATC TGGCTGTTTG   1320

GGCCTGCAAC TACCGGGAAG ACCAACATCG CGGAGGCCAT AGCCCACACT GTGCCCTTCT   1380

ACGGGTGCGT AAACTGGACC AATGAGAACT TTCCCTTCAA CGACTGTGTC GACAAGATGG   1440

TGATCTGGTG GGAGGAGGGG AAGATGACCG CCAAGGTCGT GGAGTCGGCC AAAGCCATTC   1500

TCGGAGGAAG CAAGGTGCGC GTGGACCAGA AATGCAAGTC CTCGGCCCAG ATAGACCCGA   1560

CTCCCGTGAT CGTCACCTCC AACACCAACA TGTGCGCCGT GATTGACGGG AACTCAACGA   1620

CCTTCGAACA CCAGCAGCCG TTGCAAGACC GGATGTTCAA ATTTGAACTC ACCCGCCGTC   1680

TGGATCATGA CTTTGGGAAG GTCACCAAGC AGGAAGTCAA AGACTTTTTC CGGTGGGCAA   1740

AGGATCACGT GGTTGAGGTG GAGCATGAAT CTACGTCAA AAAGGGTGGA GCCAAGAAAA   1800

GACCCGCCCC CAGTGACGCA GATATAAGTG AGCCCAAACG GGTGCGCGAG TCAGTTGCGC   1860

AGCCATCGAC GTCAGACGCG GAAGCTTCGA TCAACTACGC AGACAGGTAC CAAAACAAAT   1920

GTTCTCGTCA CGTGGGCATG AATCTGATGC TGTTTCCCTG CAGACAATGC GAGAGAATGA   1980

ATCAGAATTC AAATATCTGC TTCACTCACG GACAGAAAGA CTGTTTAGAG TGCTTTCCCG   2040

TGTCAGAATC TCAACCCGTT TCTGTCGTCA AAAAGGCGTA TCAGAAACTG TGCTACATTC   2100

ATCATATCAT GGGAAAGGTG CCAGACGCTT GCACTGCCTG CGATCTGGTC AATGTGGATT   2160

TGGATGACTG CATCTTTGAA CAATAAATGA TTTAAATCAG GTATGGCTGC CGATGGTTAT   2220

CTTCCAGATT GGCTCGAGGA CACTCTCTCT GAAGGAATAA GACAGTGGTG GAAGCTCAAA   2280

CCTGGCCCAC CACCACCAAA GCCCGCAGAG CGGCATAAGG ACGACAGCAG GGTCTTGTG    2340

CTTCCTGGGT ACAAGTACCT CGGACCCTTC AACGGACTCG ACAAGGGAGA GCCGGTCAAC   2400

GAGGCAGACG CCGCGGCCCT CGAGCACGAC AAAGCCTACG ACCGGCAGCT CGACAGCGGA   2460

GACAACCCGT ACCTCAAGTA CAACCACGCC GACGCGGAGT TCAGGAGCG CCTTAAAGAA    2520

GATACGTCTT TTGGGGGCAA CCTCGGACGA GCAGTCTTCC AGGCGAAAAA GAGGGTTCTT   2580

GAACCTCTGG GCCTGGTTGA GGAACCTGTT AAGACGGCTC CGGGAAAAAA GAGGCCGGTA   2640

GAGCACTCTC CTGTGGAGCC AGACTCCTCC TCGGGAACCG GAAAGGCGGG CCAGCAGCCT   2700

GCAAGAAAAA GATTGAATTT TGGTCAGACT GGAGACGCAG ACTCAGTACC TGACCCCCAG   2760

CCTCTCGGAC AGCCACCAGC AGCCCCCTCT GGTCTGGGAA CTAATACGAT GGCTACAGGC   2820

AGTGGCGCAC CAATGGCAGA CAATAACGAG GGCGCCGACG GAGTGGGTAA TTCCTCCGGA   2880

AATTGGCATT GCGATTCCAC ATGGATGGGC GACAGAGTCA TCACCACCAG CACCCGAACC   2940

TGGGCCCTGC CCACCTACAA CAACCACCTC TACAAACAAA TTTCCAGCCA ATCAGGAGCC   3000

TCGAACGACA ATCACTACTT TGGCTACAGC ACCCCTTGGG GGTATTTTGA CTTCAACAGA   3060
```

```
TTCCACTGCC ACTTTTCACC ACGTGACTGG CAAAGACTCA TCAACAACAA CTGGGGATTC    3120

CGACCCAAGA GACTCAACTT CAAGCTCTTT AACATTCAAG TCAAAGAGGT CACGCAGAAT    3180

GACGGTACGA CGACGATTGC CAATAACCTT ACCAGCACGG TTCAGGTGTT TACTGACTCG    3240

GAGTACCAGC TCCCGTACGT CCTCGGCTCG GCGCATCAAG GATGCCTCCC GCCGTTCCCA    3300

GCAGACGTCT TCATGGTGCC ACAGTATGGA TACCTCACCC TGAACAACGG GAGTCAGGCA    3360

GTAGGACGCT CTTCATTTTA CTGCCTGGAG TACTTTCCTT CTCAGATGCT GCGTACCGGA    3420

AACAACTTTA CCTTCAGCTA CACTTTTGAG GACGTTCCTT TCCACAGCAG CTACGCTCAC    3480

AGCCAGAGTC TGGACCGTCT CATGAATCCT CTCATCGACC AGTACCTGTA TTACTTGAGC    3540

AGAACAAACA CTCCAAGTGG AACCACCACG CAGTCAAGGC TTCAGTTTTC TCAGGCCGGA    3600

GCGAGTGACA TTCGGGACCA GTCTAGGAAC TGGCTTCCTG GACCCTGTTA CCGCCAGCAG    3660

CGAGTATCAA AGACATCTGC GGATAACAAC AACAGTGAAT ACTCGTGGAC TGGAGCTACC    3720

AAGTACCACC TCAATGGCAG AGACTCTCTG GTGAATCCGG GGCCCGCCAT GGCAAGCCAC    3780

AAGGACGATG AAGAAAAGTT TTTTCCTCAG AGCGGGGTTC TCATCTTTGG GAAGCAAGGC    3840

TCAGAGAAAA CAAATGTGAA CATTGAAAAG GTCATGATTA CAGACGAAGA GGAAATCGGA    3900

ACAACCAATC CCGTGGCTAC GGAGCAGTAT GGTTCTGTAT CTACCAACCT CCAGAGAGGC    3960

AACAGACAAG CAGCTACCGC AGATGTCAAC ACACAAGGCG TTCTTCCAGG CATGGTCTGG    4020

CAGGACAGAG ATGTGTACCT TCAGGGGCCC ATCTGGGCAA AGATTCCACA CACGGACGGA    4080

CATTTTCACC CCTCTCCCCT CATGGGTGGA TTCGGACTTA AACACCCTCC TCCACAGATT    4140

CTCATCAAGA ACACCCCGGT ACCTGCGAAT CCTTCGACCA CCTTCAGTGC GGCAAAGTTT    4200

GCTTCCTTCA TCACACAGTA CTCCACGGGA CACGGTCAGC GTGGAGATCG AGTGGGAGCT    4260

GCAGAAGGAA AACAGCAAAC GCTGGAATCC CGAAATTCAG TACACTTCCA ACTACAACAA    4320

GTCTGTTAAT CGTGGACTTA CCGTGGATAC TAATGGCGTG TATTCAGAGC CTCGCCCCAT    4380

TGGCACCAGA TACCTGACTC GTAATCTGTA ATTGCTTGTT AATCAATAAA CCGTTTAATT    4440

CGTTGCAGTT GAACTTTGGT CTCTGCGTAT TTCTTTCTTA TCTAGTTTCC ATGGCTACGT    4500

AGATAATTAG CATGGCGGGT TAATCATTAA CTACAAGGAA CCCCTAGTGA TGGAGTTGGC    4560

CACTCCCTCT CTGCGCGCTC GCTCGCTCAC TGAGGCCGGG CGACCAAAGG TCGCCCGACG    4620

CCCGGGCTTT GCCCGGGCGG CCTCAGTGAG CGAGCGAGCG CGCAGAGAGG GAGTGGCCAA    4680
```

(2) INFORMATION FOR SEQ ID NO: 2:

(i) SEQUENCE CHARACTERISTICS:
        (A) LENGTH: 2658 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

```
ATGGGATGTC TTGGGAATCA GCTGCTTATC GCGCTCTTGC TAGTAAGTGT TTTAGAGATT      60

TGTTGTGTTC AATATGTAAC AGTATTCTAT GGTGTACCAG CATGGAAGAA TGCGACAATT     120

CCCCTCTTCT GTGCAACCAA GAATAGGGAC ACTTGGGGAA CAACACAATG CTTGCCAGAT     180

AATGATGATT ACTCAGAATT GGCAATCAAT GTCACAGAGG CTTTTGATGC TTGGGATAAT     240

ACAGTCACAG AACAAGCAAT AGAGGATGTG TGGAACCTCT TGAAACATC  CATTAAGCCC     300

TGTGTAAAAC TCACCCCACT ATGTATAGCA ATGAGATGTA ATAAAACTGA GACAGATAGG     360
```

```
TGGGGTTTGA CAGGAAACGC AGGGACAACA ACAACAGCAA TAACAACAAC AGCAACACCA    420

AGTGTAGCAG AAAATGTTAT AAATGAAAGT AATCCGGGCA TAAAAAATAA TAGTTGTGCA    480

GGCTTGGAAC AGGAGCCCAT GATAGGTTGT AAATTTAACA TGACAGGGTT AAATAGGGAC    540

AAAAAGAAAG AATATAATGA AACATGGTAT TCAAGAGATT TAATCTGTGA GCAGTCAGCG    600

AATGAAAGTG AGAGTAAATG TTACATGCAT CATTGTAACA CCAGTGTTAT TCAAGAATCC    660

TGTGACAAGC ATTATTGGGA TGCTATTAGA TTTAGATACT GTGCACCGCC AGGTTATGCT    720

TTGCTTAGGT GTAATGATTC AAATTATTTA GGCTTTGCTC CTAACTGTTC TAAGGTAGTG    780

GTTTCTTCAT GCACAAGAAT GATGGAGACG CAAACCTCTA CTTGGTTTGG CTTCAATGGT    840

ACTAGGGCAG AAAATAGAAC ATACATTTAT TGGCATGGCA AAAGTAATAG AACCATAATT    900

AGCTTGAATA AGTATTATAA TCTAACAATG AGATGTAGAA GACCAGAAAA TAAGACAGTT    960

TTACCAGTCA CCATTATGTC AGGGTTGGTC TTCCATTCGC AGCCCATAAA TGAGAGACCA    1020

AAACAGGCCT GGTGCTGGTT TGAAGGAAGC TGGAAAAAGG CCATCCAGGA AGTGAAGGAA    1080

ACCTTGGTCA ACATCCCAG GTATACGGGA ACTAATGATA CTAGGAAAAT TAATCTAACA     1140

GCTCCAGCAG GAGGAGATCC AGAAGTCACT TTTATGTGGA CAAATTGTCG AGGAGAATTC    1200

TTATATTGCA AAATGAATTG GTTTCTTAAT TGGGTAGAGG ACAGAGACCA AAAGGGTGGC    1260

AGATGGAAAC AACAAAATAG GAAAGAGCAA CAGAAGAAAA ATTATGTGCC ATGTCATATT    1320

AGACAAATAA TCAACACGTG GCACAAAGTA GGCAAAAATG TATATTTGCC TCCTAGGGAA    1380

GGAGACCTGA CATGCAATTC CACTGTAACT AGTCTCATAG CAGAGATAGA TTGGATCAAT    1440

AGCAATGAGA CCAATATCAC CATGAGTGCA GAGGTGGCAG AACTGTATCG ATTGGAGTTG    1500

GGAGATTACA AATTAATAGA GATTACTCCA ATTGGCTTGG CCCCCACAAG TGTAAGAAGG    1560

TACACCACAA CTGGTGCCTC AAGAAATAAG AGAGGGTCT TTGTGCTAGG GTTCTTGGGT     1620

TTTCTCGCGA CAGCAGGTTC TGCAATGGGC GCGGCGTCCG TGACGCTGTC GGCTCAGTCC    1680

CGGACTTTGT TGGCTGGGAT AGTGCAGCAA CAGCAACAGC TGTTGGATGT GGTCAAGAGA    1740

CAACAAGAAT TGTTGCGACT GACCGTCTGG GGAACTAAGA ACCTCCAGAC TAGAGTCACT    1800

GCTATCGAGA AGTACCTGAA GGATCAGGCG CAGCTAAATT CATGGGGATG TGCTTTTAGG    1860

CAAGTCTGTC ACACTACTGT ACCATGGCCA AATGAAACAT TGGTGCCTAA TTGGAACAAT    1920

ATGACTTGGC AAGAGTGGGA AAGACAGGTT GACTTCCTAG AGGCAAATAT AACTCAATTA    1980

TTAGAAGAAG CACAAATTCA GCAAGAAAAG AATATGTATG AATTGCAAAA ATTAAATAGC    2040

TGGGATATCT TTGGCAATTG GTTTGACCTT ACTTCTTGGA TAAGATATAT ACAATATGGT    2100

GTACTTATAG TTCTAGGAGT AATAGGGTTA AGAATAGTAA TATATGTAGT GCAAATGTTA    2160

GCTAGGTTAA GACAGGGTTA TAGGCCAGTG TTCTCTTCCC CTCCCGCTTA TGTTCAGCAG    2220

ATCCCTATCC ACAAGGGCCA GGAACCGCCA ACCAAAGAAG GAGAAGAAGG AGACGGTGGA    2280

GACAGAGGTG GCAGCAGATC TTGGCCTTGG CAGATAGAAT ATATTCATTT CCTGATCCGC    2340

CAGTTGATAC GCCTCTTGAC TTGGCTATTC AGCAGCTGCA GGGATTGGCT ATTGAGGAGC    2400

TACCAGATCC TCCAACCAGT GCTCCAGAGC CTCTCAACGA CGTTGCAAAG AGTCCGTGAA    2460

GTCATCAGAA TTGAAATAGC CTACCTACAA TATGGGTGGC GCTATTTCCA AGAAGCAGTA    2520

CAAGCGTGGT GGAAACTTGC GCGAGAGACT CTTGCAAGCG CGTGGGGAGA CATATGGGAG    2580

ACTCTGGGAA GGGTTGGAAG AGGGATACTC GCAATCCCTA GGCGCATCAG GCAAGGGCTT    2640

GAGCTCACTC TCTTGTGA                                                 2658
```

(2) INFORMATION FOR SEQ ID NO: 3:

(i) SEQUENCE CHARACTERISTICS:
        (A) LENGTH: 2571 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

```
ATGAGAGTGA AGGGGATCAG GAGGAATTAT CAGCACTGGT GGGGATGGGG CACGATGCTC    60

CTTGGGTTAT TAATGATCTG TAGTGCTACA GAAAAATTGT GGGTCACAGT CTATTATGGG   120

GTACCTGTGT GGAAAGAAGC AACCACCACT CTATTTTGTG CATCAGATGC TAAAGCATAT   180

GATACAGAGG TACATAATGT TTGGGCCACA CAAGCCTGTG TACCCACAGA CCCCAACCCA   240

CAAGAAGTAG AATTGGTAAA TGTGACAGAA AATTTTAACA TGTGGAAAAA TAACATGGTA   300

GAACAGATGC ATGAGGATAT AATCAGTTTA TGGGATCAAA GCCTAAAGCC ATGTGTAAAA   360

TTAACCCCAC TCTGTGTTAC TTTAAATTGC ACTGATTTGA GGAATACTAC TAATACCAAT   420

AATAGTACTG CTAATAACAA TAGTAATAGC GAGGGAACAA TAAAGGGAGG AGAAATGAAA   480

AACTGCTCTT TCAATATCAC CACAAGCATA AGAGATAAGA TGCAGAAAGA ATATGCACTT   540

CTTTATAAAC TTGATATAGT ATCAATAGAT AATGATAGTA CCAGCTATAG GTTGATAAGT   600

TGTAATACCT CAGTCATTAC ACAAGCTTGT CCAAAGATAT CCTTTGAGCC AATTCCCATA   660

CACTATTGTG CCCCGGCTGG TTTTGCGATT CTAAAATGTA ACGATAAAAA GTTCAGTGGA   720

AAAGGATCAT GTAAAAATGT CAGCACAGTA CAATGTACAC ATGGAATTAG GCCAGTAGTA   780

TCAACTCAAC TGCTGTTAAA TGGCAGTCTA GCAGAAGAAG AGGTAGTAAT TAGATCTGAG   840

AATTTCACTG ATAATGCTAA AACCATCATA GTACATCTGA ATGAATCTGT ACAAATTAAT   900

TGTACAAGAC CCAACTACAA TAAAAGAAAA AGGATACATA TAGGACCAGG GAGAGCATTT   960

TATACAACAA AAAATATAAT AGGAACTATA AGACAAGCAC ATTGTAACAT TAGTAGAGCA  1020

AAATGGAATG ACACTTTAAG ACAGATAGTT AGCAAATTAA AGAACAATT  TAAGAATAAA  1080

ACAATAGTCT TTAATCAATC CTCAGGAGGG GACCCAGAAA TTGTAATGCA CAGTTTTAAT  1140

TGTGGAGGGG AATTTTTCTA CTGTAATACA TCACCACTGT TTAATAGTAC TTGGAATGGT  1200

AATAATACTT GGAATAATAC TACAGGGTCA ATAACAATA  TCACACTTCA ATGCAAAATA  1260

AAACAAATTA TAAACATGTG GCAGGAAGTA GGAAAAGCAA TGTATGCCCC TCCCATTGAA  1320

GGACAAATTA GATGTTCATC AAATATTACA GGGCTACTAT TAACAAGAGA TGGTGGTAAG  1380

GACACGGACA CGAACGACAC CGAGATCTTC AGACCTGGAG GAGGAGATAT GAGGGACAAT  1440

TGGAGAAGTG AATTATATAA ATATAAAGTA GTAACAATTG AACCATTAGG AGTAGCACCC  1500

ACCAAGGCAA AGAGAAGAGT GGTGCAGAGA GAAAAAAGAG CAGCGATAGG AGCTCTGTTC  1560

CTTGGGTTCT TAGGAGCAGC AGGAAGCACT ATGGGCGCAG CGTCAGTGAC GCTGACGGTA  1620

CAGGCCAGAC TATTATTGTC TGGTATAGTG CAACAGCAGA ACAATTTGCT GAGGGCCATT  1680

GAGGCGCAAC AGCATATGTT GCAACTCACA GTCTGGGCA  TCAAGCAGCT CCAGGCAAGA  1740

GTCCTGGCTG TGGAAAGATA CCTAAAGGAT CAACAGCTCC TGGGGTTTTG GGGTTGCTCT  1800

GGAAAACTCA TTTGCACCAC TACTGTGCCT TGGAATGCTA GTTGGAGTAA TAAATCTCTG  1860

GATGATATTT GGAATAACAT GACCTGGATG CAGTGGGAAA GAGAAATTGA CAATTACACA  1920

AGCTTAATAT ACTCATTACT AGAAAAATCG CAAACCCAAC AAGAAAAGAA TGAACAAGAA  1980
```

-continued

| | | | | | |
|---|---|---|---|---|---|
| TTATTGGAAT | TGGATAAATG | GGCAAGTTTG | TGGAATTGGT | TTGACATAAC | AAATTGGCTG | 2040 |
| TGGTATATAA | AAATATTCAT | AATGATAGTA | GGAGGCTTGG | TAGGTTTAAG | AATAGTTTTT | 2100 |
| GCTGTACTTT | CTATAGTGAA | TAGAGTTAGG | CAGGGATACT | CACCATTGTC | GTTGCAGACC | 2160 |
| CGCCCCCCAG | TTCCGAGGGG | ACCCGACAGG | CCCGAAGGAA | TCGAAGAAGA | AGGTGGAGAG | 2220 |
| AGAGACAGAG | ACACATCCGG | TCGATTAGTG | CATGGATTCT | TAGCAATTAT | CTGGGTCGAC | 2280 |
| CTGCGGAGCC | TGTTCCTCTT | CAGCTACCAC | CACAGAGACT | TACTCTTGAT | TGCAGCGAGG | 2340 |
| ATTGTGGAAC | TTCTGGGACG | CAGGGGGTGG | GAAGTCCTCA | AATATTGGTG | GAATCTCCTA | 2400 |
| CAGTATTGGA | GTCAGGAACT | AAAGAGTAGT | GCTGTTAGCT | TGCTTAATGC | CACAGCTATA | 2460 |
| GCAGTAGCTG | AGGGGACAGA | TAGGGTTATA | GAAGTACTGC | AAAGAGCTGG | TAGAGCTATT | 2520 |
| CTCCACATAC | CTACAAGAAT | AAGACAGGGC | TTGGAAAGGG | CTTTGCTATA | A | 2571 |